(12) United States Patent
Van Halsema

(10) Patent No.: US 12,235,199 B2
(45) Date of Patent: Feb. 25, 2025

(54) MEASURING SYSTEM FOR FOODSTUFFS

(71) Applicant: LANVI PATENT B.V., Maassluis (NL)

(72) Inventor: Frans Emo Diderik Van Halsema, Maassluis (NL)

(73) Assignee: LANVI PATENT B.V., Maassluis (NL)

( * ) Notice: Subject to any disclaimer, the term of this patent is extended or adjusted under 35 U.S.C. 154(b) by 104 days.

(21) Appl. No.: 17/765,653

(22) PCT Filed: Sep. 25, 2020

(86) PCT No.: PCT/NL2020/050594
§ 371 (c)(1),
(2) Date: Mar. 31, 2022

(87) PCT Pub. No.: WO2021/066644
PCT Pub. Date: Apr. 8, 2021

(65) Prior Publication Data
US 2022/0357259 A1  Nov. 10, 2022

(30) Foreign Application Priority Data
Oct. 1, 2019  (NL) ...................................... 2023921

(51) Int. Cl.
*G01N 21/51* (2006.01)
*G01N 11/12* (2006.01)
(Continued)

(52) U.S. Cl.
CPC ............. *G01N 11/12* (2013.01); *G01N 21/51* (2013.01); *G01N 21/8507* (2013.01); *G01N 33/04* (2013.01); *G01N 2201/062* (2013.01)

(58) Field of Classification Search
CPC .......... G01N 11/12; G01N 21/51; G01N 33/04
See application file for complete search history.

(56) References Cited

U.S. PATENT DOCUMENTS

2007/0266776 A1* 11/2007 Liberatore ........... G01N 11/142
  73/54.23
2011/0166802 A1*  7/2011 Kong ................. G01N 33/2847
  702/50

FOREIGN PATENT DOCUMENTS

AT    518797 A1 *  1/2018 ............. G01N 11/14
DE   4206107 A1 *  9/1993 ......... G01N 21/8507
(Continued)

OTHER PUBLICATIONS

International Search Report mailed on Feb. 9, 2021 in PCT/NL2020/050594 filed on Sep. 25, 2020.
(Continued)

*Primary Examiner* — Jamel E Williams
(74) *Attorney, Agent, or Firm* — Oblon, McClelland, Maier & Neustadt, L.L.P.

(57) ABSTRACT

A measuring system for determining and/or monitoring the quality of a liquid or viscous foodstuff, including a housing with an interior space for a product container for the foodstuff, a heating and cooling device, and a control unit. The product container has a lid with a thermometer probe projecting into the product container, and a transparent wall. The housing has a light source, an optical sensor for registering light entering the product container via the foodstuff, and a measuring device for rheological properties of the foodstuff. The control unit is connected to the thermometer, the heating and cooling device, the light source, the optical sensor and the measuring device, and is designed to set a predetermined time-temperature program in the interior space, and to repeatedly perform measurements on the foodstuff to determine a measured value of said foodstuff, and for storing and/or exporting and/or processing the measured values.

19 Claims, 1 Drawing Sheet

(51) Int. Cl.
*G01N 21/85* (2006.01)
*G01N 33/04* (2006.01)

(56) References Cited

FOREIGN PATENT DOCUMENTS

WO    WO 2004/025283 A1    3/2004
WO    WO-2008118618 A1 * 10/2008   ............. G01N 11/10
WO    WO-2015000695 A1 *  1/2015   ............. G01N 21/49

OTHER PUBLICATIONS

NL Search Report dated Jun. 23, 2020 in Application NL 2023921 filed on Oct. 1, 2019.

* cited by examiner

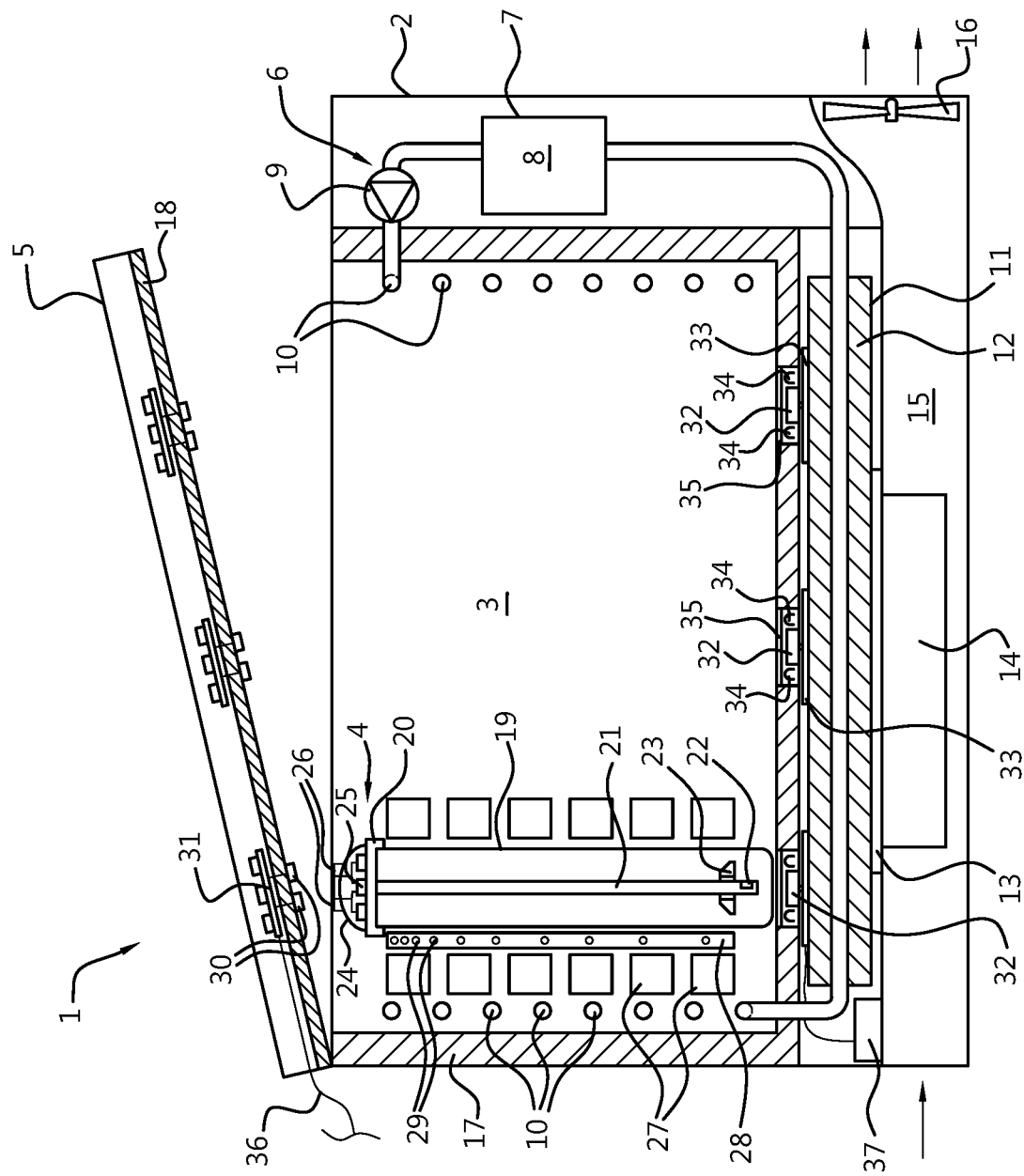

MEASURING SYSTEM FOR FOODSTUFFS

The present invention relates to a measuring system for automatically determining and/or monitoring the quality of a liquid or viscous foodstuff, and comprising at least one product container for accommodating such a foodstuff therein, a housing with an interior space for accommodating the product container, a heating and cooling device for heating and cooling the interior space, and a control unit for controlling the measuring system.

Such measuring systems are known per se, in particular in the food industry, where it is important to know the properties of the products well, so that the necessary warranties can be given with regard to food safety, but also with regard to other product properties. When developing such products, many tests thus have to be performed. In addition, there is currently a significant shift in consumer preference with regard to, in particular, animal proteins, Many consumers want products in which these have been replaced by vegetable proteins. However, this results in new methods of preparation due to the different properties, Partly for this reason, a very large number of additional tests with associated measurements are necessary.

A drawback of the existing systems is the fact that these largely rely on measurements performed by humans. Partly because of the large numbers of measurements to be performed and the great importance of reliable measurements, this is a situation which is not always satisfactory.

It is therefore an object of the present invention to provide a measuring system of the kind mentioned in the introduction which overcomes the abovementioned drawback at least partly. In particular, it is an object to provide an automatic measuring system which is routinely able to measure many significant properties under controlled circumstances.

The invention achieves this object, at least partly, by means of a measuring system according to claim 1, in particular a measuring system for automatically determining and/or monitoring the quality of a liquid or viscous foodstuff, and comprising at least one product container for accommodating such a foodstuff therein, a housing with an interior space for accommodating the product container, a heating and cooling device for heating and cooling the interior space, and a control unit for controlling the measuring system, wherein the product container is provided with a lid with a probe which projects into the product container and is provided with a thermometer, and a wall, at least part of which is optically transparent, wherein the housing furthermore comprises a light source for emitting light through said part of the wall into the product container, and an optical sensor for registering the light emanating from the product container, furthermore comprising a first measuring device for rheological properties of said foodstuff, in particular a viscosity meter, wherein the control unit is operatively connected to the thermometer, the heating and cooling device, the light source, the optical sensor and the first measuring device, and is configured for the heating and cooling device setting a predetermined time-temperature program in the interior space for a time period, and controlling at least one of the first measuring device, and the light source and optical sensor, for automatically repeatedly performing an associated measurement on said foodstuff in the product container during said time period, for thereby determining a measured value relating to said foodstuff, and for storing and/or exporting and/or processing the measured values.

Herein, the present invention provides a measuring system which can automatically test significant properties, at least is able to determine associated measured values, such as rheological properties, for example viscosity values, and/or optical properties, such as turbidity or change in colour. What is important is that the measuring system autonomously and automatically controls a time-temperature program, so that the products accommodated in the measuring system undergo the same time-temperature program. This is important because products, when used by, in particular, consumers are also subjected to varied temperatures. For example, dairy products which have to be kept refrigerated after production are transported, distributed (during which time they may also spend some time on a loading platform in the sun), transported by the consumer in a hot car, placed in the refrigerator, placed on a table (possibly in the sun), placed back in the fridge, etc. In order to find out the properties and in particular the stability (shelf life) of products at these greatly fluctuating temperatures, and this in a reliable, repeatable way, a great number of measurements are required. The measured values necessary for studying and classification are automatically collected under the most varied (temperature) circumstances. If desired, these measured values may be exported automatically, for example to an external computer or data center, or they are processed in situ by the control unit. Thus, a very efficient and reliable measuring system is provided which facilitates the development of new products.

In the present invention, the lid may be a releasable lid, but may also be a lid to be used for fastening once, such as with a snap connection.

Specific embodiments are described in the dependent claims and in the following part of the introduction of the description.

In particular, the product container has a dimensionally stable wall with a transparent part or a flexible wall of transparent plastic. In the former case, a transparent window is provided in a container which may, incidentally, be nontransparent. As a result thereof, it is in each case possible to make an optimum choice for the base material of the container and for the material for the transparent window, for example with regard to strength, or transmission value or transmission wavelength range, respectively. Materials such as glass, quarts, polycarbonate, etc. may be used here as optically transparent material, while metals, plastics, etc., but again glass, quartz, etc. may be used as material for the container(s). In the latter case, this may, in particular, be a kind of bag made of transparent plastic. This offers advantages with regard to contact with the wall of the housing and makes it possible for the wall to be (much) thinner, thereby providing improved heat conduction.

The optical sensor is not particularly limited per se and may comprise, for example, a photodetector or the like which measures light that is reflected, diffused or even emitted by the foodstuff in the container. In this way, it is possible to obtain information about a spectrum of the foodstuff, such as a colour or a fluorescent content, etc., or a change over time in the colour, this content, etc. in embodiments, the optical sensor comprises a camera. By means of such an optical sensor, it is possible to obtain much more optical information. In particular, a camera is able to detect deposits or another inhomogeneity which is usually an indication of a deterioration in quality or at least of a change. More advantageously, the camera is therefore arranged under the container, in which case at least the underside of the container is made of transparent material. However, it is also possible to arrange the camera above or next to the container, such as below and next to the container.

In particular, the light source comprises one or more LEDs. Not only do these have the advantage of a very low generation of heat, so that the temperature of the foodstuff in the container is only influenced to a minimal degree, but they are also available in many different designs with a very stable and readily controllable emission in various wavelength bands. In this way, it is possible to collect optical information about the foodstuff in an optimum manner by choosing one or more suitable LED(s).

In embodiments, the light source is arranged around the optical sensor. This results in a symmetrical arrangement, which is preferable in many situations. In addition, this means that little or no direct light impinges on the optical sensor, which suppresses glare. In addition, it is thus possible to arrange both the optical sensor and the light source under the container(s) or even outside the space for the containers, if the wall of the space between the camera, light source and the transparent window is also transparent. The advantage is then, for example, that the heat of the optical sensor also remains at least largely outside the container.

Alternatively or additionally, the light source is arranged on the container above the probe, and the light source comprises at least one light conductor, such as an optical fiber, next to or through the probe. Light which is generated with such a light source, in general incidentally: optical radiation, which also includes (near) infrared and ultraviolet light, is injected in a light conductor, such as an optical fiber. An important advantage of the light conductor is that in this way, heat generated by the light source (or control unit thereof) and/or the sensor (or control unit thereof) will very effectively remain distant from the foodstuff, so that the measurements cannot be influenced thereby. The optical fiber is, for example, a part of the probe and also projects into the container, advantageously into the foodstuff when used. Preferably, the light conductor in this case extends to just above the bottom of the container, that is to say within at most 20% of the height of the container. This ensures extension into the foodstuff when the container is used in a standard way, so that the light to be emitted by the light conductor can be injected into the foodstuff efficiently.

The first measuring device serves to measure rheological properties of the foodstuff in the container. These comprise, in particular, the viscosity, or sometimes also a viscosity, because this may depend on, for example, the speed, and certainly also on the temperature. The viscosity of a foodstuff is a significant property, and changes therein, or not meeting the predetermined requirements, is an important quality criterion for, for example, yoghurt, quark, etc. The first measuring device as such is not particularly limited, but, in embodiments, the first measuring device comprises a magnetic body, a controllable electromagnetic drive for the body, and a detection system for detecting a displacement of the body, comprising a plurality of proximity sensors, in particular Hall sensors, wherein, in use, the body is situated in the container and is displaceable in the container on account of the drive. By means of such an arrangement ('falling ball viscometer), it is possible, in particular for viscous substances, to measure the viscosity using the final (falling) velocity, the acceleration, etc., of the magnetic body while it falls through the foodstuff. In this case, the magnetic body passes the proximity sensors and these in turn emit a signal from which the control device can determine the position of the magnetic body.

In particular, the body is situated around the probe. Here, it is easy to make the arrangement (rotationally) symmetrical, which has advantages when calculating the viscosity value. Furthermore, the positioning of the body with respect to the drive is known and constant, and thus readily controllable.

In embodiments, the drive comprises a plurality of individually energisable coils which are wound around the container and stacked in a stack, wherein the control unit is configured for individually energising the coils, in such a way that the body in the container is displaced. In particular, energising takes place according to a predetermined pattern. It is known per se to energise and move a magnetic body using a coil, but said embodiment offers a significant advantage with the often viscous products to be tested, since the individual coils in a stack can assume the task of displacing the body from each other. In this way, displacement of the body can still be ensured, even with very viscous liquids, such as quark, mayonnaise or thick yoghurt. It is then also possible to determine high viscosity values by increasing the power exerted by the individual coils.

The particular pattern used may be determined as a function of a product property of the foodstuff to be tested. For example, the pattern is quicker, and the is associated (final) velocities higher, at low viscosity values than at high viscosity values. In a completely different application, it is also possible to mix the foodstuff by alternately moving the body up and down. To this end, it is sufficient to reverse the order of the pattern and/or to reverse polarity of the coils.

The embodiments described thus far offer the possibility of determining a number of significant basic properties, such as viscosity, colour and deposits, as well as changes therein, as a function of temperature and of time, and from those, for example, indirectly shelf life as well. Nevertheless, it is advantageous to gather more information about the foodstuff. In particular, the measuring system to this end comprises at least one additional sensor for determining an additional measured value relating to said foodstuff in the product container. Important examples of such additional sensors are conductivity or (for electrochemical impedance spectroscopy) DS sensors, pH sensors etc. Obviously, the or each additional sensor may be chosen from the wide range of available sensors depending on the required property/properties.

On the basis of changes in the value of one or more of the measured properties, in particular the colour, or when deposits occur, the control unit is able to automatically assess one or more properties of the product, such as whether or not the latter meets the quality requirements. In specific embodiments, the control unit is configured for in each case processing at least one measured value and/or optional additional measured value determined during the time-temperature program by generating an alarm signal when, and/or registering a lapsed time period (in particular from the start of the measurement or the beginning of a start criterion) until the determined measured value(s), and/or, optionally, the additional measured value(s), satisfies(/satisfy) a predetermined criterion, in particular a decay criterion. This offers the possibility of determining product properties, such as shelf life, entirely automatically, that is to say independently from human actions and errors, and also continuously, and therefore more accurately.

The invention will be explained in more detail below by means of one or more exemplary embodiments, as well as the drawing. In the latter, the sole FIGURE shows a diagrammatic sectional view of a measuring system according to the invention.

The FIGURE shows a diagrammatic sectional view of a measuring system 1 according to the invention. The measuring system 1 comprises a housing 2 with an interior space 3 and one product container 4, as well as a lid 5.

In addition, a cooling device is denoted by reference numeral 6 which comprises a storage container 7 for refrigerant 8, a pump 9, a pipe system 10, a cold is buffer 11 with a phase change material 12, a Peltier cooler 13, a heatsink 15, a ventilation space 15 and a fan 16. Insulating material 17 and 18, respectively, is provided in the housing 2 and the lid 5, respectively.

The product container 4 comprises a cup 19 and a container lid 20 with a probe 21 with a thermometer 22. A magnetic body is denoted by reference numeral 23. Furthermore, a sensor sphere 24 surrounds optical sensors 25 and is provided with contacts 26. Electromagnetic coils 27 surround a carrier 28 with Hall sensors 29. The lid 5 is provided with countercontacts 30 to electronics 31.

Cameras 32 are connected to respective camera control units 33. Optionally, a plurality of LEDs 34 are arranged around the camera and above them a protective glass 35 is placed. Finally, reference numeral 36 denotes a connection to the outside and reference numeral 37 denotes a control unit for the system 1.

The illustrated system 1 comprises a housing 2 and lid 5 of, for example, metal or plastic, which surround an interior space 3 which is insulated with insulating material 17 and 18. A plurality of product containers 4 may be placed in the interior space 3, in the illustrated example three, of which only one is shown for the sake of clarity.

By means of the cooling system 6, the interior space 3 may be brought to a desired temperature by the control unit 35. It should be stressed here that the cooling system 6 is additionally provided with a heating device (not shown here), such as electrical heating wires or the like. These can bring the interior space to a higher desired temperature in a manner which is known per se. Subsequently, after some desired time period, the control unit 35 may actuate the cooling part, that is to say the cooling system 6, to bring the interior space 3 to a desired lower temperature. To this end, the cooling system 6 comprises a storage container 7 with a refrigerant 8, such as glycol, which serves to transfer heat. To this end, a pump 9 pumps the refrigerant 8 through a, for example spiral-shaped, pipe system 10 around the interior space 3. In this case, the refrigerant 8 may dissipate its heat to the phase change material (PCM) 12 in the cold buffer 11. The PCM 12 may simply be water/ice, wherein the heat absorbed from the refrigerant 8 makes the ice melt to form water, but advantageously, the PCM may also be a different material. A particular drawback of water is the fact that it expands when it solidifies, and that the melting point is at 0° C., or below if additives were added. However, numerous other PCMs are available which do not have these drawbacks and which have phase transitions which are, for example, at a temperature between 5 and 40° C., For example, the interior space may be heated first to a pasteurisation temperature, such as 72° C., or also a sterilisation temperature, such as around 130° C. Important other temperatures are use temperatures to which foodstuffs may be exposed, such as heating up to 30 to 40° C. on a loading platform in the sun or on the table of a consumer, and then back to a cooling temperature of 4-6° C. It is also possible to measure how the properties of the foodstuff change over time at one and the same temperature, such as 6, 8 or 10° C. In this case, it is very important that any changes can be stopped in all cases, at least be prevented as much as possible, when a certain desired temperature regime has been completed, To this end, it is important that the foodstuff can be cooled quickly to in particular a desired end temperature, such as a temperature at which no (significant) further change occurs, in particular with regard to sugars and/or bacterial growth. Therefore, an active cooling system is desired. Should the case arise, the thermometer 22 measures the temperature of the foodstuff in the product container 4, with which signal the control unit 35 can actuate the cooling system 6 and or the heating system.

For this active cooling system, a refrigerant is thus pumped around in the cooling circuit with pipe system 10 by means of the pump 9, The PCM 12 in the cold buffer 11 is itself cooled by means of any known cooling device, such as a heat pump or a Joule-Thomson cooling system. However, it is advantageous to choose a compact cooling system, because space is limited or may be expensive, in particular in a laboratory. In addition, moving parts are not always desired. For this reason, a Peltier cooling system 13 is advantageous, as it is compact and does not contain moving parts itself. However, in this case a fan 16 is provided which guides air past a heatsink 14 via a ventilation space 15, so that the heat can be dissipated from the system 1 in an efficient manner.

At the bottom of the interior space 3, in the bottom thereof, cameras 32 are arranged which have an upwardly directed image field and thus form an image of the underside of their respective product container 4, However, to this end, the latter has to be made either from a transparent material, such as glass or polycarbonate, or also be flexible, such as PE film, or have a transparent window. The associated control and/or processing electronics may be provided under the insulation 17, so that it is protected against the changing and sometimes extreme temperatures. Using the camera, it is possible to produce an image of the foodstuff in the product container 4, In particular, it is thus possible to observe changes in the colour and/or deposits, which may be important to monitor and measure the quality overall, or certain product properties in particular, as a function of temperature and/or time.

Optionally, a light source is provided to support the operation of the camera 32, in this case in the form of a plurality of LEDs 34, The LEDs may emit light of the same or different colours and, as they are provided around the camera, they can use the same electronics platform. The LEDs 34 can emit light into the product in the product container 19 via the protective glass 35, which is made, for example, from borosilicate glass, fused glass or another translucent and preferably chemical-, temperature- and scratch-resistant material Emitted light which has subsequently been reflected by the product can be detected by the camera 32 and then be analysed by the control unit 37, or can be transmitted externally for further processing via the connection 36. It is also still possible to provide still other sensors (not shown here) in addition to the camera 32, such as InGaAs or Si sensors, which offer better sensitivity in, for example, the (N)IR range than most cameras 32.

Another possibility is to provide a light source in the lid 20 of the product container 4. There, light conductors, such as optical fibers, may be provided in the sensor sphere 24, where the emitted light may be injected, and the probe 21 may be inserted. Reflected light or diffused light can then also be collected by one or more light conductors in the probe and sent to the sensor sphere 24, where sensors 25 can measure the light in order to thus obtain additional information about colour and, for example, transparency. A portion of the light will be reflected and a portion will be transmitted, so that the respective coefficients for the foodstuff can be determined by the control unit therefrom.

Furthermore, a viscosity-measuring device is also provided to measure the viscosity and changes therein of the foodstuff in the respective product container 4, The viscosity-measuring device comprises a series of coils 27 which are arranged around the product container 4, as well as a series of Hall sensors 29 on a carrier 28 and a magnetic body 23 around the probe 22. This is in itself similar to the known "falling ball" measurement. The control unit 35 energises the individual coils 27 in a suitable pattern. The magnetic body 23 is attracted by respective magnetic fields of the individual coils 27 and possibly even, after polarity reversal, repelled, as a result of which it moves and moves, for example, upwards. When it has arrived in the upper part of the product container 4, for example, all coils which are still energised are switched off, after which the body 23 will start to drop. When it moves past the Hall sensors 29, these will emit a position-dependent signal which can be processed by the control unit 35 to a drop position as a function of time and thus as a measuring system for the speed, and therefrom the viscosity of the foodstuff in the product container. If the viscosity is very high, as is the case with emulsions, yoghurts, etc., then the viscosity may also be determined from the speed which the body 23 may reach on account of the fields of the coils 27. An important additional advantage of the described magnetic system is the fact that this can also be used to mix the foodstuff in the product container 4, in particular by repeatedly and/or quickly moving the magnetic body up and down. This mixing makes it possible, for example, to cancel sedimentation as much as possible, and to then measure the product properties, Consumers often do something similar with the respective product, such as "shake well before use".

In particular, it is also advantageous if the sensor device(s) is/are built into the respective lid of the product container. Thus, it is even possible, in principle, to perform different measurements on one and the same product by changing the lid for a lid with another sensor device.

Advantageously, the sensor device(s) is/are replaceably fittable, such as in the lid of the product container. This means that either the sensor device is fittable in and removable from the lid, or that the lid is replaceable in its entirety, including the sensor device or the probe. To this end An important advantage thereof is that it is very simple to fit the required sensor device(s) for each experiment and for each product in the system, and to automatically perform the associated measurements. This provides a high degree of flexibility.

In the exemplary embodiment described so far, one product container 4 is provided and illustrated in the interior space 3. In practice, associated coils 27, a carrier 28 with Hall sensors 29, a camera 32, etc., only some of which are shown here for the sake of clarity, will in each case be provided for each available location for a product container in the interior space 3, of which three are shown here. Also, different numbers of available locations may be provided, such as two, four, five, etc.

In use, one or more product containers 4 are filled with a foodstuff to be measured, for example with different recipes or also the same, for redundant measurements. Subsequently, the lid 5 of the system 1 is closed. As a result thereof, the insulation 17 and 18 around the interior space 3 with the product container(s) 4 seals. This also protects the electronics 31 against temperature variations. In addition, it is also possible to provide the sensors 25 in the sensor sphere 24 with insulation, At the same time, the countercontacts 30 in the lid make contact with the contacts 26 on the lid 20 of the product container, so that the electronics 31 can ensure control of the optional sensors 25, the thermometer 22, etc. Furthermore, it is possible to design the contacts 26 and/or the electronics of the product container situated behind them in such a way that the electronics 31, or the control unit 35 which is operatively connected thereto, is able to recognise the product container and, if desired, its contents. This further reduces the risk of errors by human operators.

Furthermore, a desired time-temperature profile is input into the control unit 35 by a user, such as via the connection 34, which may obviously also be designed as a wireless connection (Bluetooth® or the like) or a USB connection, SD card or even via the lid 5 provided on the product container 4, etc. The control unit 35 will subsequently actuate the heating and/or the cooling system 6, under the control of the temperature measured by the thermometer 22, in order to set the desired profile. At certain times, random or regular, the control unit 35 will cause the one or more sensors 22, 25, 29, 32 to perform one or more measurements. The measured data which are thus collected may be stored by the control unit for future use. They may also be sent to an external data storage or data processing facility via the connection 34. They may also be processed by the control unit 35, for example in order to monitor if one or more product parameters fall outside a desired range. In this case, examples thereof may be checking the colour of the product or the transparency/deposits by means of the camera 32 or the viscosity. Should the value be outside a desired range, the control unit can emit an alarm signal, again for example via the connection 34, If desired, the remaining part of the time-temperature profile may be cancelled. Alternatively, it is possible to determine how long it took before the value moved outside the desired range for the foodstuff in the respective product container 4. This makes it possible, for example, to determine a shelf life.

The illustrated embodiment is by no means intended to be limiting for the invention, but only serves to explain it. The scope of protection of the invention is determined by the attached claims.

The invention claimed is:

1. A measuring system for automatically determining and/or monitoring a quality of a liquid or viscous foodstuff, comprising:
   at least one product container for accommodating the foodstuff therein,
   a housing with an interior space for accommodating the product container,
   a heating and cooling device for heating and cooling the interior space of the housing, and
   a control unit for controlling the measuring system,
   wherein the product container is provided with
   a lid with a probe which projects into the product container and is provided with a thermometer, and
   a wall, at least part of which is optically transparent,
   wherein the housing further comprises:
   a light source for emitting light through said optically transparent part of the wall into the product container, and
   comprising a camera for registering the light emanating from the product container, furthermore comprising a first measuring device for rheological properties of the foodstuff,
   wherein the control unit is operatively connected to the thermometer, the heating and cooling device, the light source, the camera and the first measuring device, and is configured for:
   setting a predetermined time-temperature program in the interior space for a time period, and controlling at least one of the first measuring device, and the light source and camera, for automatically repeatedly performing an associated measurement on the foodstuff in the product container during the time period, for thereby determining a measured value relating to the foodstuff, and for storing and/or exporting and/or processing the measured values.

2. The measuring system according to claim 1, wherein the product container has a dimensionally stable wall with a transparent part.

3. The measuring system according to claim 1, wherein the light source comprises one or more LEDs.

4. The measuring system according to claim 3, wherein the light source is arranged around the camera.

5. The measuring system according to claim 3, wherein the light source is arranged on the container above the probe and comprises at least one light conductor, next to or through the probe.

6. The measuring system according to claim 1, wherein the first measuring device further comprises:
a magnetic body,
a controllable electromagnetic drive for the magnetic body, and
a detection system for detecting a displacement of the body, comprising a plurality of proximity sensors,
wherein during use the magnetic body is situated in the container and is displaceable in the container by the controllable electromagnetic drive.

7. The measuring system according to claim 6, wherein the magnetic body is situated around the probe.

8. The measuring system according to claim 6, wherein the controllable electromagnetic drive comprises a plurality of individually energisable coils which are wound around the container and stacked in a stack,
wherein the control unit is configured for individually energising the coils, in such a way that the body in the container is displaced.

9. The measuring system according to claim 1, further comprising at least one additional sensor for determining an additional measured value relating to said foodstuff in the product container.

10. The measuring system according to claim 1, wherein the control unit is configured for in each case processing at least one measured value determined during the time-temperature program by
generating an alarm signal when, and/or
registering a lapsed time period until the determined measured value.

11. The measuring system according to claim 1, wherein the first measuring device is a viscosity meter.

12. The measuring system according to claim 1, wherein the product container has a flexible wall of transparent plastic.

13. The measuring system according to claim 6, wherein the plurality of proximity sensors are Hall sensors.

14. The measuring system according to claim 8, wherein the container is displaced in a predetermined pattern.

15. The measuring system according to claim 10, wherein the control unit is configured for processing at least one additional measured value determined during the time-temperature program by generating an alarm signal when, and/or registering a lapsed time period until the additional measured value satisfied a predetermined criterion.

16. The measuring system according to claim 15, wherein the predetermined criterion is a decay criterion.

17. The measuring system according to claim 5, wherein the at least one light conductor is an optical fiber.

18. A measuring system for automatically determining and/or monitoring a quality of a liquid or viscous foodstuff, comprising:
at least one product container for accommodating the foodstuff therein,
a housing with an interior space for accommodating the product container,
a heating and cooling device for heating and cooling the interior space of the housing, and
a control unit for controlling the measuring system,
wherein the product container is provided with
a lid with a probe which projects into the product container and is provided with a thermometer, and
a wall, at least part of which is optically transparent,
wherein the housing further comprises:
a light source comprising one or more LEDs for emitting light through said optically transparent part of the wall into the product container, and
an optical sensor for registering the light emanating from the product container, furthermore comprising a first measuring device for rheological properties of the foodstuff,
wherein the control unit is operatively connected to the thermometer, the heating and cooling device, the light source, the optical sensor and the first measuring device, and is configured for:
setting a predetermined time-temperature program in the interior space for a time period, and
controlling at least one of the first measuring device, and the light source and optical sensor, for automatically repeatedly performing an associated measurement on the foodstuff in the product container during the time period, for thereby determining a measured value relating to the foodstuff, and for storing and/or exporting and/or processing the measured values.

19. A measuring system for automatically determining and/or monitoring a quality of a liquid or viscous foodstuff, comprising:
at least one product container for accommodating the foodstuff therein,
a housing with an interior space for accommodating the product container,
a heating and cooling device for heating and cooling the interior space of the housing, and
a control unit for controlling the measuring system,
wherein the product container is provided with
a lid with a probe which projects into the product container and is provided with a thermometer, and
a wall, at least part of which is optically transparent,
wherein the housing further comprises:
a light source for emitting light through said optically transparent part of the wall into the product container, and
an optical sensor for registering the light emanating from the product container, furthermore comprising a first measuring device for rheological properties of the foodstuff,
wherein the control unit is operatively connected to the thermometer, the heating and cooling device, the light source, the optical sensor and the first measuring device, and is configured for:
setting a predetermined time-temperature program in the interior space for a time period, and
controlling at least one of the first measuring device, and the light source and optical sensor, for automatically repeatedly performing an associated measurement on the foodstuff in the product container during the time period, for thereby determining a measured value relating to the foodstuff, and for storing and/or exporting and/or processing the measured values, and wherein the first measuring device further comprises,
- a magnetic body,
- a controllable electromagnetic drive for the magnetic body, and
- a detection system for detecting a displacement of the body, comprising a plurality of proximity sensors, wherein during use the magnetic body is situated in the container and is displaceable in the container by the controllable electromagnetic drive.

* * * * *